(12) United States Patent
Howett et al.

(10) Patent No.: US 6,309,848 B1
(45) Date of Patent: Oct. 30, 2001

(54) HUMAN XENOGRAFTS FOR MICROBICIDE TESTING AND ANATOMICAL MODELING

(75) Inventors: Mary K. Howett, Harrisburg; John W. Kreider, Palmyra, both of PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/624,318

(22) Filed: Jul. 24, 2000

Related U.S. Application Data

(62) Division of application No. 09/426,144, filed on Oct. 22, 1999.

(51) Int. Cl.$^7$ ............................. C12N 5/00; C12N 15/00; A61K 48/00
(52) U.S. Cl. ............................. 435/9.2; 424/9.1; 424/9.2; 435/7.21; 800/3
(58) Field of Search ............................. 435/7.21; 800/3; 424/9.2, 9.1

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,814,268 | 3/1989 | Kreider et al. | 435/239 |
| 5,071,757 | 12/1991 | Kreider et al. | 435/239 |
| 5,227,298 * | 7/1993 | Weber et al. | 435/178 |
| 5,811,632 * | 11/1998 | Brandsma | 800/2 |

OTHER PUBLICATIONS

White, et al. Eye, vol. 9, No. 2, pp. 185–189, 1995.*
"AIDS Among Persons Aged≧50 Years—United States, 1991–1996," Morbidity and Mortality Weekly Report 4(2):21–47 (1998).
Arvin and Prober, "Herpes Simplex Viruses," in Murray et al. (eds.), *Manual of Clinical Microbiology*, (6th ed.), ASM Press, Washington, D.C., pp. 876–883 (1995).
Biro et al., "Knowledge of Gonorrhea in Adolescent Females with a History of STD," *Clin. Pediatr.*, 33:601–605 (1994).
Calis, S., et al. "A non–antibiotic antimicrobial mixture (C31G): evaluation of the antimicrobial efficiency of C31G on vaginal cultures.", *Boll. Chim. Farmaceut.* 131:335–338 (1992).
Corner, A.M., et al., "C31G, a new agent for oral use with potent antimicrobial and antiadherence properties." *Antimicro. Agents Chemo.* 32:350–353 (1988).
Crotchfelt et al., "Detection of *Neisseria gonorrhoeae* and *Chlamydia trachomatis* in Genitourinary Specimens from Men and Women by a Coamplification PCR Assay," *J. Clin. Microbiol.*, 35:1536–1540 (1997).
Division of STD Prevention, Sexually Transmitted Disease Surveillance, 1996, U.S. Department of Health and Human Services, Public Health Service, Centers for Disease Control and Prevention, Sep., 1997.

Durst et al., "A papillomavirus DNA from a cervical carcinoma and its prevalence in cancer biopsy samples from different geographic regions," *Proc. Natl. Acad. Sci.*, 80:3812–3815 (1983).
Famighetti, *1996 World Almanac and Book of Facts*, World Almanac Books, Mahwah, New Jersey, (1995), p.840.
Galloway et al., "Carcinoma of the Larynx After Irradiation for Papilloma," *Archives of Otolaryngology* 72:289–294 (1960).
Gillis, S., et al., "Biochemical and biological characterization of lymphocyte regulatory molecules. V. Identification of an interleukin 2–producing human leukemia T cell line." *J. Exp. Med.* 152:1709–1719 (1980).
Herold et al., "Sulfated Carbohydrate Compounds Prevent Microbial Adherence by Sexually Transmitted Disease Pathogens," *Antimicrob. Agent. Chemother.* 41(12):2776–278 (1997).
Hicks, R.R., et al., "Inactivation of HTLV–III/LAV–infected cultures of normal human lymphocytes by nonoxynol–9 in vivo.", *Lancet* 2(8469–8470):1422–1423 (1985).
Hodgins et al., "An immunohistochemical study of androgen, oestrogen and progesterone receptors in the vulva and vagina." *Br. J. Obstet. Gyn.* 105:216–222 (1998).
Ikenberg et al., "Human Papillomavirus type–16–related DNA in Genital Bowen's Disease and in Bowenoid Papulosis," *Int. J. Cancer*, 32:563–565 (1983).
Kreiss, J., et al., "Efficacy of nonoxynol–9 contraceptive sponge use in preventing heterosexual acquisition of HIV in Nairobi prostitutes." *JAMA* 268 (4):477–482 (1992).
Orth et al., "Characteristics of the Lesions and Risk of Malignant Conversion Associated with the Type of Human Papillomavirus Involved in Epidermodysplasia Verruciformis," *Cancer Res.*, 39:1074–1082 (1979).
Phillips, "Intravaginal formulations to prevent HIV infection," *Perspect. Drug Disc. Design* 5:213–224 (1996).
Rapp, F. et al., "Synergistic effect of human leukocyte interferon and nonoxynol–9 against herpes simplex virus type 2." *Antimicro. Agnt. and Chemo.*, 28:449–451 (1985).
Roddy, R.E., et al., "A controlled trial of nonoxynol 9 film to reduce male–to–female transmission of sexually transmitted diseases." *N. Engl. J. Med.*, 339(8):504–10 (1998).
Rosenthal et al., "Seroprevalence of Herpes Simplex Virus Types 1 and 2 and Cytomegalovirus in Adolescents," *Clin. Infect. Dis.*, 24:135–139 (1997).

(List continued on next page.)

*Primary Examiner*—Jill D. Martin
(74) *Attorney, Agent, or Firm*—Medlen & Carroll, LLP

(57) ABSTRACT

A method for screening candidate antimicrobial compounds is described that utilizes a human vaginal xenograft engrafted in a non-human host. The method may be performed by using pathogen inoculated human vaginal xenografts in order to screen a wide range of candidate antimicrobials administered topically or systemically.

15 Claims, 5 Drawing Sheets

(3 of 5 Drawing Sheet(s) Filed in Color)

OTHER PUBLICATIONS

Smith, S.D., et al., "Monoclonal antibody and enzymatic profiles of human malignant T–lymphoid cells and derived cell lines.", *Cancer Res.* 44:5657–5660 (1984).

Stanberry, *Understanding Herpes*, University Press of Mississippi, Jackson, MS [1998].

Sundstrom, C., et al., "Establishment and characterization of a human histiocytic lymphoma cell line (U937)." *Int. J. Cancer* 17:565–577 (1976).

Tsuchiya, S., et al., "Establishment and characterization of a human acute monocytic leukemia cell line (THP–1)." *Int. J. Cancer* 26:171–176 (1980).

Wright, J.R., et al., "Pulmonary surfactant protein A stimulates chemotaxis of alveolar macrophage." *Am. J. Physiol.* 264:(4 Pt 1) L338–344 (1993).

Kent et al., "Screening for Chlamydia trachomatis Infection in a Sexually Transmitted Disease Clinic: Comparison of Diagnostic Teats with Clinical and Historical Risk Factors," *Sexually Transmitted Diseases* Jan.–Mar. (1988).

* cited by examiner

HUMAN XENOGRAFTS FOR MICROBICIDE TESTING AND ANATOMICAL MODELING

This application is a Divisional Application of pending application Ser. No. 09/426,144, filed on Oct. 22, 1999.

FIELD OF THE INVENTION

The present invention relates generally to the incorporation of human tissue xenografts into methods for modeling the physiology and anatomy of vaginal epithelium, studying fastidious vaginal pathogens, evaluating the pharmacology of vaginally reactive agents, and, in particular, evaluating the efficacy of candidate anti-microbial agents and, more particularly, to screening the capacity of candidate microbicides, in human vaginal xenografts, to prevent and/or treat sexually transmitted diseases.

BACKGROUND OF THE INVENTION

I. Sexually Transmitted Diseases

Sexually transmitted diseases (STDs), referring to diseases that are most often transmitted by direct sexual contact, remain an increasingly serious public health problem in the United States, as well as other countries. Indeed, these diseases present a public health crisis. See e.g., Herold et al., Antimicrob. Agent. Chemother., 41:2776–278 (1997). For Example, according to the *Summary of Notifiable Diseases*, five of the ten most prevalent infectious diseases are STDs. Summary of Notifiable Diseases—United States, 1996. MMWR Morb. Mortal. Wkly. Rep. p. 45 (1997). Additionally, The World Health Organization has estimated that 125 million new cases of major bacterial and viral STDs occur each year (See, Herold, supra, at p. 2776). In terms of human cost, the World Bank has estimated that for adults of 15 to 44 years of age, STDs (other than human immunodeficiency virus (HIV) infection) are the second leading cause of healthy life lost in women (See, Herold, supra, at p. 2776). Women are especially at risk as many STDs are asymptomatic and there is a high morbidity rate associated with untreated disease (See e.g., Biro et al., Clin. Pediatr., 33:601–605 [1994]). Of these diseases, significant etiologic agents are human papillomavirus (HPV), herpes simplex virus type 2 (HSV-2), HIV, *Chlamydia trachomatis, Neissena gonorrhoeae*, and *Treponema pallidum*.

A. Human Papillomavirus

Human papillomaviruses are a heterogeneous group of viruses that induce epithelial or fibroepithelial proliferations of skin or mucosa. Over 80 types of human papillomavirus (HPV) are recognized, many of which are associated with distinctive lesions. Specific diseases associated with HPV infection, such as common warts, epidermodysplasia verruciformis, and genital warts (condylomata), correlate with specific HPV types. For example, HPV-1 has been shown to produce skin warts, and HPV-11 has been shown to produce genital warts. The latter type can also produce warts on the vocal cords of newborns who have been infected by their mothers. Such warts are a serious problem to the newborns because they may threaten breathing and must be surgically removed.

Recent studies have implicated HPVs in the development of premalignant and malignant lesions of the skin (Ikenberg et al., Int. J. Cancer, 32: 563–565, 1983; Orth et al., Cancer Res., 39: 1074–1082, 1979), uterine cervix (Durst et al., Proc. Natl. Acad. Sci., 80: 3812–3815, 1983), and larynx (Galloway et al., Arch. Otol., 72: 289–294, 1960). For example, HPV-16 and HPV-18 has been isolated and molecularly cloned from cervical carcinoma cells and these HPV types are strongly associated with cervical carcinomas. It is significant to note that HPV's only grow in differentiating human epithelium. Notably, methods of propagating and detecting HPV have been described in U.S. Pat. No. 4,814,268 and U.S. Pat. No. 5,071,757 hereby incorporated by reference.

B. HIV

Since its recognition in 1981, the acquired immunodeficiency syndrome (AIDS) has become a catastrophic pandemic. The worldwide prevalence of the human immunodeficiency virus (HIV) infection has been estimated at more than 30,000,000. In addition, an estimated of 1.5 million children have been infected with HIV (Famighetti, 1996 *World Almanac and Book of Facts*, World Almanac Books, Mahwah, N.J., [1995], p.840). In 1996, the incidence of AIDS-opportunistic illnesses in the United States, was approximately 6,390 per 100,00 population for those 50 years of age and older; for those 13–49 years of age, the incidence was approximately 50,340 per 100,000 ("AIDS Among Persons Aged 50 Years—United States, 1991–1996," Morbidity and Mortality Weekly Report, Jan. 23, 1998). The AIDS pandemic is a premiere public health concern. Individuals who are at high risk of HIV infection are also at risk of infection by other sexually transmitted pathogens. Similarly, individuals at risk for non-HIV sexually transmitted pathogens are also at high risk for HIV infection.

Additionally, it is significant to note that women comprise the most rapidly increasing population of the AIDS epidemic. Furthermore, the site of HIV entry (e.g., vagina, cervix, etc) in women is poorly defined. Therefore, protection of vaginal and anal epithelium from HIV entry [beyond the current questionable effective and often irritating application of Nonoxynol-9 (N-9)] is desirable.

C. *Chlamydia Trachomatis*

Considering epidemiological data for *C. trachomatis*, the reported number of cases in the U.S. for 1996 was 490,000 (i.e., a rate of 194.5 per 100,000 persons (this rate was based on reports from 49 states, and the District of Columbia, although only cases from New York City are included in the figures for New York). See, Division of STD Prevention, Sexually Transmitted Disease Surveillance, 1996, U.S. Department of Health and Human Services, Public Health Service, Centers for Disease Control and Prevention, September, 1997. This rate exceeds that of all other notifiable infectious diseases in the U.S. This represents an increase from 47.8 per 100,000 to 194.5, for the time period of 1987 to 1996. For the period of 1995 to 1996, the rates increased 2% (i.e., from 313.2 cases per 100,000 to 318.6). For women, the rate (321.5 per 100,000) was over five times that reported in men. In terms of the female population infected, the highest rates of chlamydia infection occurred in adolescents. The rates are highest in the 15 to 19 year old population with 2,068.6 cases per 100,000, followed by the 20 to 24 year old age group, with 1,485.2 cases. In addition, the prevalence of *C. trachomatis* infection is highest in economically disadvantaged young women. Untreated *C. trachomatis* infections often present debilitating sequelae such as pelvic inflammatory disease (PID), which can lead to infertility, ectopic pregnancy, and chronic pelvic pain.

D. HSV-2

Herpes simplex virus 2 (HSV-2) causes a significant amount of morbidity and mortality. The prevalence of HSV-2 infection increases at adolescence, with infection rates of 15 to more than 50% in some adult populations (See e.g., Arvin and Prober, "Herpes Simplex Viruses," in Murray et al. (eds.), *Manual of Clinical Microbiology*, (6th ed.), ASM Press, Washington, D.C., pages 876–883 [1995]; Rosenthal et al., Clin. Infect. Dis., 24:135–139 [1997]; and Stanberny, *Understanding Herpes*, University Press of Mississippi, Jackson, Miss. [1998]).

Many cases of HSV-2 infection are subclinical. Indeed, primary infections are often entirely asymptomatic. In addition, despite the apparently universal establishment of latency following infection with either virus, many individuals with past HSV infections do not experience symptomatic recurrences. However, asymptomatic recurrences do occur, making prevention of the transmission HSV-2 in the population very difficult. Indeed, HSV-2 infections may cause acute, latent, and recurrent genital infections. In immunocompromised patients, the lesions associated with HSV-2 may be severe. In addition, infected pregnant women may shed HSV-2, thereby (at times) fatally infecting their newborns.

E. *Neisseria Gonorrhea*

In the United States alone, conservative estimates suggest that about one million people per year are infected with *N. gonorrhea*. Worldwide, there is an estimated annual incidence of 25 million cases of *N. gonorrhoeae* (Crotchfelt et al., J. Clin. Microbiol., 35:1536–1540 [1997]). Although the number of gonorrhea cases has steadily decreased since the establishment of gonorrhea control programs in the mid-1970s, the problem is not solved. Gonorrhea remains a significant cause of morbidity. Infection with *N. gonorrhoeae* remains a major case of PID, tubal infertility, ectopic pregnancy, and chronic pelvic pain. Furthermore, epidemiologic evidence strongly suggests that gonococcal infections facilitate HIV transmission. Rates of gonorrhea in women are particularly high in adolescents, with the highest rates observed in 15 to 19 year olds. For men, the highest rate was observed in the 20 to 24 year old age group. In addition, the percentage of men with repeated infection within a one year period has increased from a low of 13.8% in 1994, to 15.7% in 1996. Of additional concern is the growing number of *N. gonorrhoeae* isolates with decreased susceptibility to penicillin and/or tetracycline, and ciprofloxacin.

Although there has been considerable work on *N. gonorrhoeae* vaccines, none are available. In the case of gonorrhoea, it is unlikely that a vaccine will be easily developed because of the rapid and effective antigenic modulation which is one of the hallmarks of *N. gonorrhoea* (Phillips, Perspect. Drug Disc. Design 5:213–224 [1996]).

F. *Treponema pallidum*

Infection with *Treponema pallidum*, the etiologic agent of syphilis is of particular concern during pregnancy, as untreated early syphilis results in perinatal death in up to 40% of cases. If the syphilitic infection is acquired during the four years prior to pregnancy, the fetus is infected in over 70% of cases. Furthermore, syphilis facilitates transmission of HIV and may be particularly significant in areas of the United States (e.g., the South), where both infection rates are high.

In sum, clinical pathologies attributable to STDs are profound. STDs cause acute and chronic disease, infertility, and (in some cases) cancer. Vaccines, which are costly and time-consuming to develop, are unavailable for the treatment of most STDs. This is especially true in the case of HIV where the absence of a vaccine has necessitated the employ of alternative therapeutic strategies, such as retrovirus triple therapy (e.g., AZT, DDI, etc.) to lower virus burden. However, it costs approximately $15,000 (U.S.) annually to maintain a patient on retrovirus triple therapy. This expense, therefore, renders this therapeutic option practically unavailable to Third World populations where HIV is most prevalent. Indeed, the sum of all available STD therapeutics is effective against only a limited number of susceptible pathogens. Furthermore, this limited therapeutic arsenal is largely confined to proprietary formulations which are costly for the afflicted to procure.

II. Antimicrobial Agents

Antimicrobial agents act according to a variety of mechanisms. Specifically, these agents may destroy microbes, prevent their pathogenic action, or inhibit their growth. Antimicrobial agents, often referred to as anti-infective agents, are conveniently applied topically to the skin and mucous ihembranes. In some instances antimicrobial agents may be incorporated into pharmaceutical preparations suitable for intravaginal administration. Regardless of the formulation, however, desirable properties of antimicrobial agents include, but are not limited to, properties recited in Table 1.

TABLE 1

| Ideal Properties For A Candidate Antimicrobicide | |
|---|---|
| Broad Spectrum | Able to inactivate bacteria and viruses and possibly fungi |
| Fast Acting | Able to be effective within minutes of application |
| Persistent | Effective after initial application long enough to allow discreet insertion by the female; capable of being effective for more than one coitus during a single encounter |
| Inexpensive | Affordable to the poor and inhabitants of the Third World |
| Eazy to Formulate | Stable at ambient temperature; compatible and active after mixture with chemically simple and cosmetically acceptable formulations |
| Non-Toxic | Non-damaging to vulvar, vaginal, cervical or penile epithelium and possibly non-damaging to sperm; does not facilitate entry cf STDs, allows survival of beneficial Lactobacilli sp. |
| Discreet | Undetectable, or at least innocuous in order to avoid resistance to use by women or their partners. |

Topical antimicrobial agents may be directed at bacteria, viruses, fungi, and parasites (including but not limited to *Trichomona vaginalis*). Topical antimicrobial agents are convenient for vaginal application and have been successfully employed in the prevention and treatment of a number of infections including some STDs. N-9, specifically, inactivates enveloped viruses such as HSV-2 and HIV-1 in vitro. Hicks, R. R., et al., "Inactivation of HTLV-III/LAV-infected cultures of normal human lymphocytes by nonoxynol-9 in vivo.", Lancet, 2(8469–8470):1422–1423, (1985), Rapp, F. et al., "Synergistic effect of human leukocyte interferon and nonoxynol-9 against herpes simplex virus type 2." Antimicro. Agnt. and Chemo., 28:449451, (1985) and Judson, F. N., et al., "In vitro evaluations of condoms with and without nonoxynol-9 as physical and chemical barriers against *Chlamydia trachomatis*, herpes simplex virus type 2 and human immunodeficiency virus." Sex. Trans. Dis. 16:51–56, (1989). However, N-9 has not been proven to prevent transmission to women of some of the most deadly STDs, most notably, HIV. Roddy, R. E., et al., "A controlled trial of nonoxynol-9 film to reduce male-to-female transmission of sexually transmitted diseases." N. Engl. J. Med. 339(8) :504–10, (1998). Additionally, N-9 may cause irritation and ulceration in some people, thereby increasing STD susceptibility via trans-ulcer inoculation of pathogens or by increasing the number of proliferative cells in regenerative hyperplasia. Kreiss, J., et al., "Efficacy of nonoxynol-9 contraceptive sponge use in preventing heterosexual acquisition of HIV in Nairobi prostitutes." JAMA 268 (4):477–482 (1992). Finally, N-9 does not inactivate HPVs and, therefore, does not qualify as an antiviral microbicide vis-a-vis HPV.

In another example, C31G is an amphoteric, surface-active agent that is effective in vitro against a broad range of viral and bacterial pathogens. Calis, S., et al. "A non-antibiotic antimicrobial mixture (C31G): evaluation of the antimicrobial efficiency of C31G on vaginal cultures.", Boll. Chim. Farmaceut. 131:335–338 (1992), Corner, A. M., et al., "C31G, a new agent for oral use with potent antimicrobial and antiadherence properties." Antimicro. Agents Chemo. 32:350–353, (1988). C31G, however, is not effective against Human Papillomavirus (HPVs).

III. Existing Models for Screening STD Susceptibility to Microbicides

Currently available in vivo models for evaluating microbial efficacy are limited. HSV-2 has been propagated through inoculation into the mouse vagina. However, in the case of fastidious viruses, such as HIV and RPV, animal models for STDs are restricted to primates. Fastidious viruses have also been propagated in human tissue transplanted into non-human hosts, namely immunocompromised mice (e.g., the renal capsule). See U.S. Pat. Nos. 4,814,268 and 5,071,757 to Kreider et al. However, this prior art does not provide an experimental platform that mimics the true three dimensional architecture of human vagina in situ. Furthermore, since the prior art implants chips of human tissue to the renal capsule of a non-human host; any direct post-transplant manipulation or treatment of said chips requires traumatic surgical invasion into the peritoneum of said non-human host.

SUMMARY OF THE INVENTION

The present invention relates generally to the incorporation of human tissue xenografts into methods for evaluating the efficacy of topical or systemic candidate anti-microbial compounds and, in particular, to screening the capacity of candidate microbicides, in human vaginal xenografls, to prevent and/or treat sexually transmitted diseases.

Specifically, human vaginal xenografts have a complement of morphologic and cytochemical characteristics that are topographically similar to normal vagina. These characteristics include (but are not limited to) glycogen production, the elaboration of both estrogen receptors (ER) and progesterone receptors (PR) as well as lactoferrin (LF) production. Additionally, these xenografts elaborate glutamyl cysteine synthesis (GCS), glutathione-S-transferases (GST) and Mn and Cu/Zn superoxide dismutases (SOD) which are enzymes, found in situ in vaginal tissue, that protect vaginal epithelial cells from reactive oxygen species (ROS). By creating vaginal xenografts with such physiological and anatomical parameters of those of native in situ vaginal tissue, drugs can be evaluated against the relevant tissue architecture. This confers advantages to the screening methods claimed through the instant invention. Most importantly, the in situ growth of human tissue permits the propagation of pathogens unable to be propagated (e.g., human papillomavirus) in cell culture.

The present invention provides methods for configuring vaginal tissue removed from a human source under conditions such that a lumen is created. The present invention also recites methods for engrafting human vaginal tissue into a non-human host such that said human xenograft is sustained by the internal milieu of said non-human host. The engrafted human vaginal tissue provides a stable platform that is not rejected by the non-human host and the vaginal tissue does not necrose.

The present invention also contemplates anal epithelium, removed from a human source, configured to create a lumen substantially lined with epithelium. The present invention also recites methods for engraffing said anal epithelium comprising a lumen into a non-human host such that said human xenograft is sustained by the internal milieu of said non-human host. The engrafted human anal tissue provides a stable platform that is not rejected by the non-human host and the anal tissue does not necrose.

Methods employed to facilitate the maintenance of human xenografts in a non-human host include (but are not limited to) the use of an immunocompromised animal and the supplementation of said animal with trophic factors including (but not limited to) gonadal hormones. It is not intended the present invention be limited to any specific immunocompromised non-human host. In one embodiment, the immunocompromised host may be produced through breeding animals with genetic defects. While it is not intended that the present invention be limited to any specific immunocompromised host, in one example the immunocompromised hosts are athymic mice and SCID (severe combined immune deficiency syndrome) mice. In another embodiment, normal animals with no somatic deficiency may be treated systemically (e.g. with electromagnetic radiation, anti-sera, or chemical agents) to render said treated normal animals immunocompromised. In another embodiment, normal animals with no somatic deficiency may be treated surgically to render said treated normal animals immunocompromised. In another embodiment, normal animals may be treated with cyclosporin or other immunosuppressive agents to render said animals immunocompromised.

The present invention also provides methods for the topical or systemic treatment of said engrafted human vaginal tissue with candidate antimicrobial compounds. It is not intended that screening methods of the instant invention be limited to any specific class of candidate antimicrobial compounds. Examples of said candidate antimicrobial compounds include (but are nof limited to) detergents, surfactants, alcohols, antibiotics, antibodies, small peptide microbicides, and protein denaturants.

The present invention also provides methods for the inoculation of human vaginal tissue (both untreated and previously treated with candidate antimicrobial compounds) and the subsequent evaluation of said inoculated engrafted tissue for the transmission and infection of said sexually transmitted pathogens and, thereby, the efficacy of said candidate antimicrobial compounds.

In one embodiment, the present invention contemplates a method for screening chemical compounds comprising: a) providing, in any order: i) a non-human host; ii) a human vaginal graft comprising a lumen; iii) a candidate compound; and iv) a pathogen; b) engrafing said vaginal graft within said host to create an engrafted vaginal xenograft comprising a lumen; c) introducing said compound into said non-human host via application methods selected from topical application and systemic administration; d) inoculating said engrafted vaginal xenograft with said pathogen; and e) testing said engrafted vaginal xenograft for the presence of pathogen. It is not intended that the present invention be limited by the antimicrobial mechanism of any candidate antimicrobial compound.

DESCRIPTION OF THE FIGURES

The file of this patent contains at least one drawing executed in color. Copies of this patent with color drawings will be provided by the Patent and Trademark Office upon request and payment of the necessary fee.

DEFINITIONS

Figure 1:
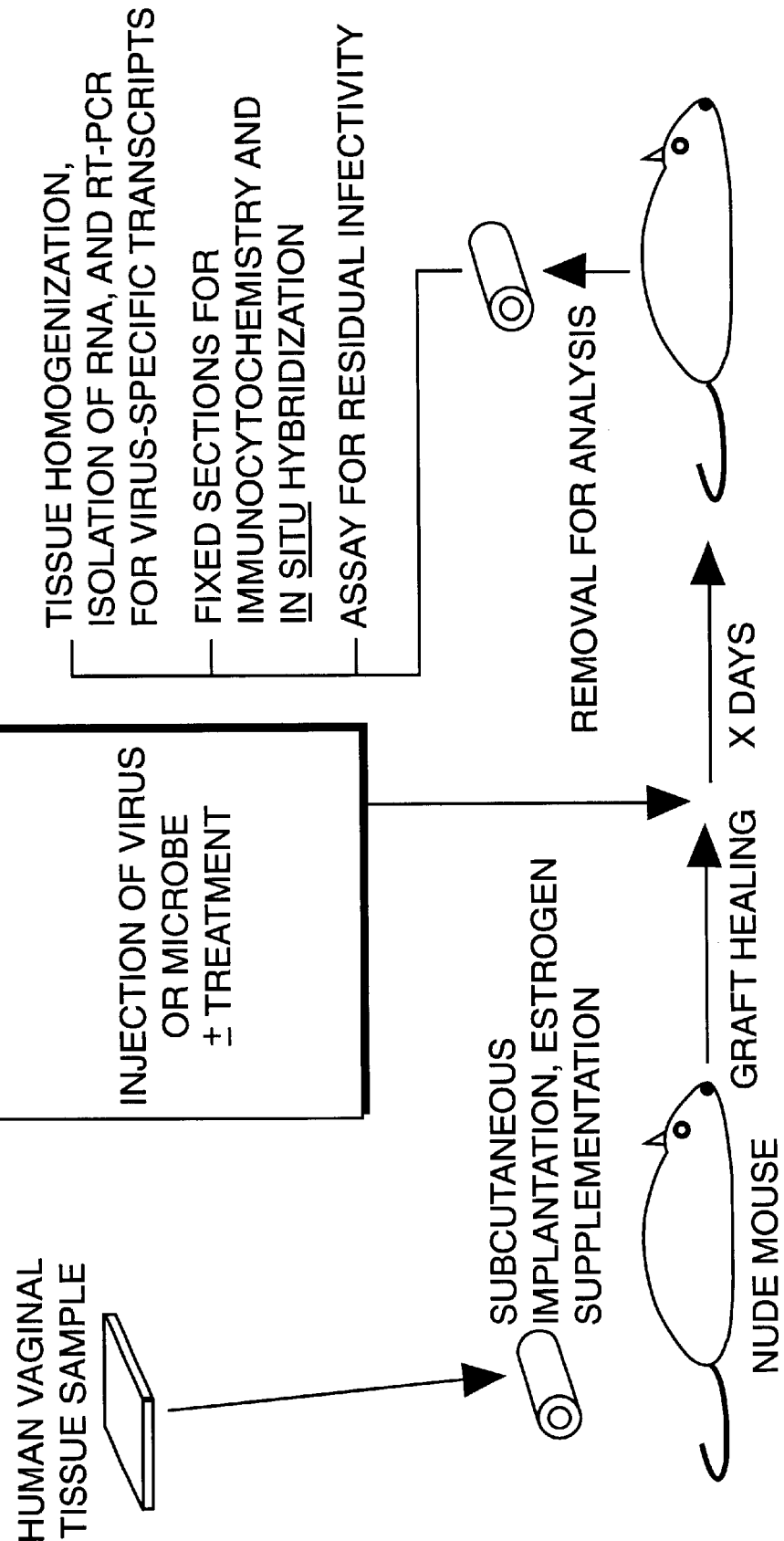
FIG. 1 presents a schematic overview of the steps comprising the screening methods recited in the instant invention including; human vaginal xenograft engraftment, graft infection, and assay for residual infectivity in said human vaginal xenografts.

To facilitate understanding of the invention set forth in the disclosure that follows, a numnber of terms are defined below.

As used herein the term "antimicrobial compound" is used in reference to any compound, substance, or molecule capable of inhibiting the growth of, or of killing microorganisms (e.g., showing activity in vitro or in vivo). It is intended that the term be used in its broadest sense, and includes, but is not limited to compounds such as antibiotics which are produced naturally or synthetically. It is also intended that the term include compounds and elements that are usefuil for inhibiting the growth of, or killing, microorgasniss. It is contemplated that compositions containing multiple compounds will find use in the present invention. For example, it is intended that the term encompass antimicrobial compositions in which a given compound is included as a component in addition to other compounds. It is not intended that the present invention be limited to any particular antimicrobial composition.

As used herein the term "candidate antimicrobial compound" is a compound suspected of having antimicrobial properties.

As used herein the term "candidate compound" is a compound of unknown antimicrobial properties.

As used herein the term "fastidious virus" is used in reference to a virus which is difficult or impossible to propagate in vitro or in laboratory animal hosts. An example of said fastidious viruses includes, but is not limited to, HPV.

As used herein the term "in situ vaginal tissue" is used in reference to the morphological and physiological profile of human vaginal tissue unencumbered by detectable anatomical abnormalities or disease states.

As used herein the term "isolated" in the context of tissue indicates tissue removed and/or separated from its natural source. A tissue graft is one embodiment of isolated tissue that has been transplanted.

As used herein the term "sexually transmitted pathogen" refers to pathogens that are most often transmitted by direct sexual contact, including kissing and vaginal intercourse, as well as anal intercourse, and other sexual activities. The term encompasses, but is not limited to, such diseases as HIV, *Chlamydia trachomatis*, human papillomavirus (HPV), herpes simplex virus, *Neisseria gonorrhea*, and *Treponema pallidum*.

As used herein the term "systemic" or "systemically" refers to the introduction of a compound into the circulatory or lymphatic system.

As used herein the term "topically" means application to the surface of the skin, mucosa, viscera, etc of a target tissue.

As used herein the term "split-thickness graft" refers to part of the epithelium and subjacent stroma.

As used herein the term "engrafted" refers to tissue surgically implanted at any anatomical site under conditions such that the internal milieu of the host may sustain said tissue.

As used herein "pharmaceutical preparation suitable for intravaginal administration" refers to a solution containing a desired compound in a pharmaceutically acceptable form for intravaginal administration. The pharmaceutical preparation may contain diluents, adjuvants and excipients, among other components, provided that those additional components neither adversely effect the preparation (e.g., they do not cause degradation of the compound) nor the recipient (e.g., they do not cause a hypersensitivity reaction).

As used herein "Nonoxynol-9" or "N-9" refers to a nonionic surfactant, in some applications, topically applied as a spermicide.

As used herein "Immunocompromised" refers to an animal with an immune system rendered deficient (as compared to a normal control animal) by an immunodeficiency disorder or by the administration of immunosuppressive agents or electromagnetic radiation.

As used herein a "Challenged Graft" refers xenobiotic tissue contacted with one or more pathogens said pathogens (in some but not all embodiments) having already been contacted with a candidate compound.

DESCRIPTION OF THE INVENTION

The present invention relates to human xenografts in animals and methods for evaluating the efficacy of topically and systemically applied compounds as microbicides. These engrafted xenografts are intended to be physiologically stable platforms capable of propagating a host of sexually transmitted pathogens including, but not limited to, fastidious viruses such as HPVs. Such a susceptible platform is a component of the methods for screening candidate antimicrobial compounds. A schematic overview of said methods for screening is presented in FIG. 1.

The description of the invention is divided into the following parts: I) Construction of Human Vaginal Xenograft And Implantation Into a Animal Host, II) Application Of Candidate Microbicides, III) Infection Of Human Vaginal Xenografts With Pathogens, IV) Detecting Pathogens In Pathogen Inoculated Human Vaginal Xenografts.

I. Construction of Human Vaginal Xenografts and Implant into an Animal Host

A. Graft Construction

The instant invention contemplates the use of human vaginal tissue in a method for the screening the antimicrobial activity of topically or systemically applied chemical compounds. In a preferred embodiment, said human vaginal tissue is conveniently obtained from surgical specimens removed during vaginal reconstructive surgeries. Tissue may also be obtained from post-mortem specimens. In one example, said tissue is obtained from the surgical repair of a vaginal prolapse. Regardless of the source, however, sections of split-thickness vaginal epithelium are cut from vaginal wall specimens. In one embodiment, the vaginal wall specimens are trimmed to a piece 2 cm wide×2 cm long×0.5 mm thick. Said vaginal wall specimens are fashioned into a rolled graft, thereby creating a lumen, such that said lumen is surrounded by the epithelial surface of the source vaginal tissue. The construction of said rolled graft comprising a lumen may be accomplished with suturing. However, in a preferred embodiment, a sutureless rolled graft is created which minimizes mechanical damage thereby creating a superior experimental platform.

Although the engraftnent site of the graft is not limited to any specific anatomical site, in one embodiment, the rolled graft (with or without sutures) is inserted into the subcutaneous space on the back of an anesthetized immunocompromised mouse and the skin wound is closed with a wound clip. Xenografts are allowed to heal into the subcutaneous space. Testing, treatment and/or infection of such grafts can be initiated at the time of grafting or at a subsequent time point depending on the desired experimental protocol.

B. Selection of an Animal Host and Introduction of a Human Graft i. Selection of an Animal Host It is not intended that the instant invention be limited by the genus or species of the non-human host. However, it is preferred that the host be immuno-compromised. A variety of non-human animals can be used as the graft recipient, including but not limited to vertebrates such as rodents; non-human primates, ovines, bovines, ruminants, lagomorphs, porcines, caprines, equines, canines, felines, aves, etc. Preferred non-human animals are selected from the rodent family including rat and mouse, most preferably mouse.

The following commercially available immunocompromised animals are preferred:

1. Athymic female mice, 3–4 weeks of age, available from Taconic Farms (Germantown, N.Y.).
2. SCID (severe combined immune deficiency syndrome) female mice, 3–4 weeks of age, available from Charles River (Wilmington, Mass.).

Athymic or SCID mice will tolerate the long-term growth of xenogenic tissues especially well. The mice are immunologically deficient and allow long-term (over 1 year) survival of the xenografts. Nonetheless, other animals are also contemplated, such as animals that have been irradiated, surgically altered, or subjected to chemical treatments such that nascent immune responses are dampened or obliterated.

ii. Introduction of a Human Graft

It is not intended that the present invention be limited to the method by which a human graft is introduced into an animal host. In a preferred embodiment, however, a transcutaneous incision is made into the dorsal aspect of a vertebrate host animal. In one example, said incision is made with scissors. In another example said incision is made with a trochar. In another example said incision is made with a scalpel. Through this incision a free space is developed between the dermis and the super muscular facia sufficient to accommodate a human vaginal tissue graft comprising a lumen substantially lined with epithelium.

In one embodiment, the opening to the lumen of said subdermally implanted vaginal tissue graft is approximated to the edge of the incision of said animal host. In this embodiment, the opening to the lumen of said implanted vaginal tissue is in fluidic communication with the environment outside the animal. In another embodiment, the opening of the lumen (in fluidic communication with the atmosphere) to said vaginal tissue graft is maintained with a stent. In one embodiment, said subcutaneous implanted vaginal tissue graft with a patent lumen is sealed at one end, thereby creating a blind lumen. In another embodiment said subcutaneous implanted vaginal tissue graft with an open lumnen is completely advanced into the subcutaneous space and the above referenced transcutaneous incision is closed, thereby sealing said tissue graft into said subdermal space.

B. Graft Maintenance

The vaginal epithelium provides the primary barrier against infection by pathogens introduced into the vagina. The normal morphology and physiology of the human vaginal epithelium, however, is responsive to modulations (associated with the menstrual cycle) of various trophic factors which include, but are not limited to, steroid hormones. For example, the vaginal epithelium tends to thicken in an estrogen rich environment while it may thin in a progesterone rich environment. While it is not essential to provide supplementation of gonadal hormones to practice the instant invention, in preferred embodiments, the non-human host is supplemented with one or more gonadal hormones at dosages which cause the engrafted tissue to present a morphology similar to that observed within in situ vaginal tissue during a given phase of the human menstrual cycle including, but not limited to, the follicular phase and the luteal phase.

Figure 5:
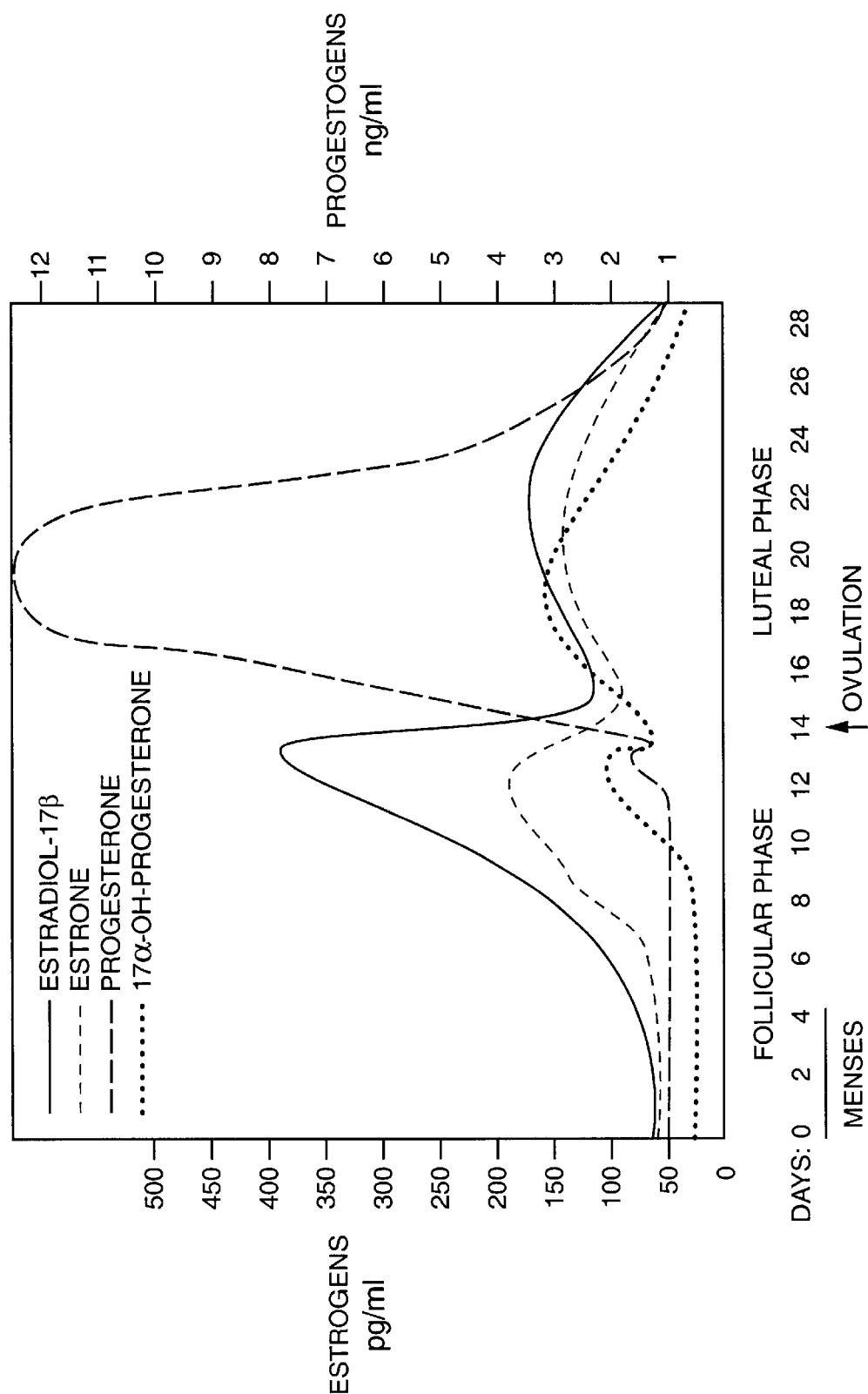
FIG. 5 presents illustrative values of mean estrogen and progesterone levels at various stages of the menstrual cycle.

Engrafting xenografts in the presence of estrogen and/or progesterone (at levels comparable to clinical values for these hormones) is desirable. While it is not intended that the present invention be limited to supplementation of gonadal hormones at any specific, FIG. 5 presents illustrative values of mean estrogen and progesterone levels at various stages of the menstrual cycle (cycle stage of hormonal responsiveness may alter susceptibility/resistance to STD's). Additionally, there are increasing numbers of women worldwide who use long-term steroid based birth control that sustain circulating levels of gonadal steroid hormones.

The hormonal supplementation of a non-human host, therefore, may recapitulate the morphology and physiology of engrafted vaginal xenografts at various phases of the human menstrual cycle or a menstrual cycle regulated by steroid contraceptives. Therefore, the present invention permits the evaluation of the efficacy of potential microbicides in vaginal xenografts which have been hormonally induced to mimic, morphologically and physiologically, equivalent in situ vaginal tissue at various stages of the menstrual cycle.

In one embodiment, the non-human host is supplemented with an estrogen. In a preferred embodiment, said estrogen is β-estradiol. In another embodiment, the host animal is supplemented with progesterone. Combination hormonal treatments are also contemplated.

i. Delivery Of Supplemental Hormones

As recited above, the supplementation of a non-human host with hormones (or other trophic factors) is not a prerequisite to practicing the instant invention. However, in those embodiments where said non-human host is supplemented with hormones or trophic factors, it is not intended that the present invention be limited to a specific delivery system. In one embodiment the delivery system is an osmotic pump. In a preferred embodiment the delivery system is silastic tubing. Silastic Brand Medical Adhesive Silicone Type A, Dow Corning (Midland, Mich.).

While it is not intended that the present invention be limited to any specific formulation or dimension of silastic tubing, in one embodiment said silastic tubing was fabricated according to the following method. Tubing (0.078 in. inner diameter by 0.125 in. outer diameter; Dow Corning, Midland, Mich.) was filled with 17β-estradiol (1,3,5 [10]-Estratriene-3, 17β(Sigma Chemical Company, St. Louis, Mo.) mixed 1:3 (w/w) with silastic 382 medical grade elastomer (Dow Corning, St. Louis, Mo.). The mixture was allowed to dry and the tubing cut, in one embodiment, to a size (approximately 2×2×1 mm) which yielded a measurable circulating estradiol concentration of about 150–200 pg/ml in mice. It may be noted that this concentration of estradiol approximates the concentration of estrogen in women during the late follicular phase of the menstrual cycle.

C. Graft Manipulation

The above referenced human vaginal xenografts may be translocated to a variety of spaces in a non-human host. It is not intended that the present invention be limited to a specific location. In one embodiment, the space is the peritoneum. In another embodiment the thoracic cavity is contemplated. In another embodiment, the renal capsule is contemplated. In another embodiment the anterior chamber of the eye is contemplated. In another embodiment the brain is contemplated. In a preferred embodiment, the subcutaneous space is contemplated. More specifically, the subdernal space of the dorsal aspect of a non-human vertebrate including (but not limited to) an immunocompromised mouse. In one example of said preferred subdennal environment, the opening of the patent lumen of a rolled human vaginal xenograft is approximated to the skin such that said lumen may be directly accessed without additional dissection. In another example of said preferred subdermal environment, said rolled human vaginal xenograft (with a patent lumen) is substantially sealed when implanted into the subdermal space. In this example said non-human host may be briefly anesthetized so that said rolled human vaginal xenograft may be manipulated through a transcutaneous incision. It is not intended that the present invention be limited to the instrument to make said transcutaneous incision. In one example the instrument is a scalpel. In another example the instrument is a scissor. Additionally, it is not intended the present invention be limited by the instrumentation used to introduce materials or agents into the lumen of said human vaginal xenografts. In one example said introducing instrument is a plastic pipet. In another example said introducing instrument is a glass pipet. In another example said introducing instrument is a trochar. In another example said introducing agent is a swab.

D. Cytochemical Characterization of the Vaginal Wall in Established Xenografts

Figure 2:
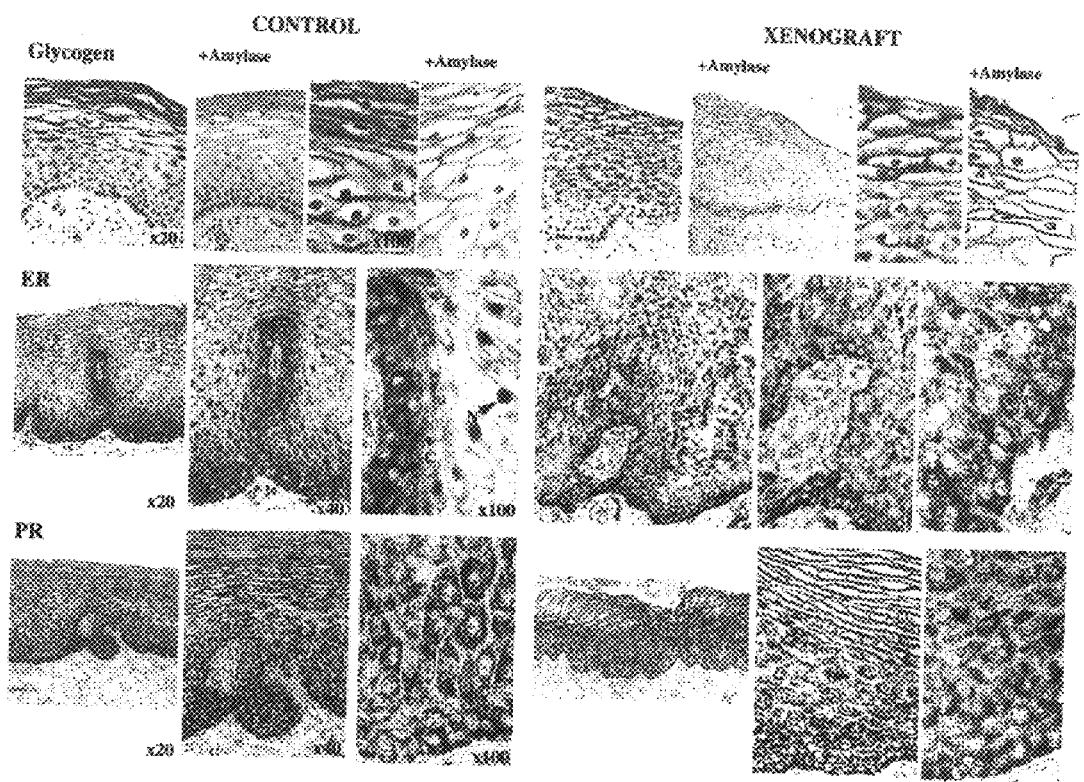
FIG. 2 presents photomicrographs from premenopausal vaginal tissue (controls) and xenografts stained for glycogen by Periodic Acid Schiff (PAS) and immunostained for ER or PR.

The engrafted xenobiotic tissue recited in the instant invention substantially recapitulates the morphology and physiology of normal human tissue observed in situ. This fidelity to normal form and function is confirmed by examining the phenotype of the xenobiotic experimental platform with respect to various facets of normal cellular expression. Specifically, said xenobiotic engrafted human vaginal tissue expresses glycogen, estrogen receptor (ER), progesterone receptor (PR), and gene products tangent to the ability of vaginal epithelium to defend against invasion by pathogens (or against environmental damage related to physical and chemical stressors) at levels comparable to ungrafted controls.

i. Glycogen, ER and PR: products known to be involved in hormonal responsiveness of the tissue A stratified squamous epithelium and glycogen production are estrogen dependent characteristics of normal human vaginal morphology and physiology essential for the control of pathogens in the vagina. As presented in FIG. 2, glycogen, ER and PR of vaginal xenografts engrafted inf estrogenized mice parallel the topography and cellular localization, as compared with sections removed from in situ normal premenopausal vagina, of these identical parameters.

Specifically samples, from histological sections of human vaginal xenografts engrafted in an immunocompromised mouse for at least 14 days, were prepared according to the following protocols. Sections (8 um) were cut from formalin fixed, paraffin embedded tissue. Specificity of Periodic Acid Schiff (PAS) stain for glycogen was demonstrated by absence of staining in sections subjected to amylase digestion. Immunocytochemistry for ER and PR was carried out following antigen retrieval (steam heating for 20 min. in citrate buffer pH 6.0) using alkaline phosphatase as reporter, bromo-chloro-indolyl phosphate as substrate and nitro-blue tetrazolium as chromogen. Specificity of ER and PR immunoreactions were confirmed by absence of reaction product in sections exposed to secondary antibodies only or to primary antibodies preabsorbed with excess ER and PR antigen, respectively (not shown). Findings were replicated using two different antibodies for each receptor.

Data from these above referenced histological preparations show that amylase sensitive glycogen is present in cell cytoplasm as revealed by PAS stain. Glycogen is localized in differentiated, superficial epithelial cells and in desquamating "dead" cells with pyknotic nuclei. ER and PR are localized to the cytoplasm and showed more intense staining in the more immature cells of the epithelium. Immunostaining for ER and PR is limited to cells in the basal and parabasal layers, consistent with histological surveys of normal vaginal tissue as reported by Hodgins et al., "An irnmmunohistochemical study of androgen, oestrogen and progesterone receptors in the vulva and vagina." Br. J. Obstet. Gyn. 105:216–222, (1998). Furthermore, ER immunostaining was observed in both cytoplasm and in nuclei (FIG. 1, ×100, N and C) while PR staining is mostly confined to the cytoplasm.

ii. Gene Products Produced in the Vagina

Tissues, such as the vagina, are equipped with an armamentarium of defenses against invasion by pathogens and against damage by environmental stressors. In order to demonstrate parity in form and finction of the xenobiotic engrafted human vaginal tissue, which is a component of the screening method claimed in the instant invention, to in situ vaginal tissue; a number of gene products were compared.

Specifically, normal sections from in situ human vagina and sections from vaginal xenografts engrafted into mice have been examined for two gene products liberated or secreted into the vaginal lumen. These gene products include LF and surfactant protein A (SP-A).

LF binds and, thereby, limits availability of free iron (Fe) in tissues and body fluids. LF is a significant marker because Fe is needed by certain cellular pathogens for replication. While the instant invention is not limited to a specific mechanism, vaginal LF exerts a bacteriostatic function that is a useful marker for factors contributing to the preservation of a normal vaginal milieu.

Figure 3:
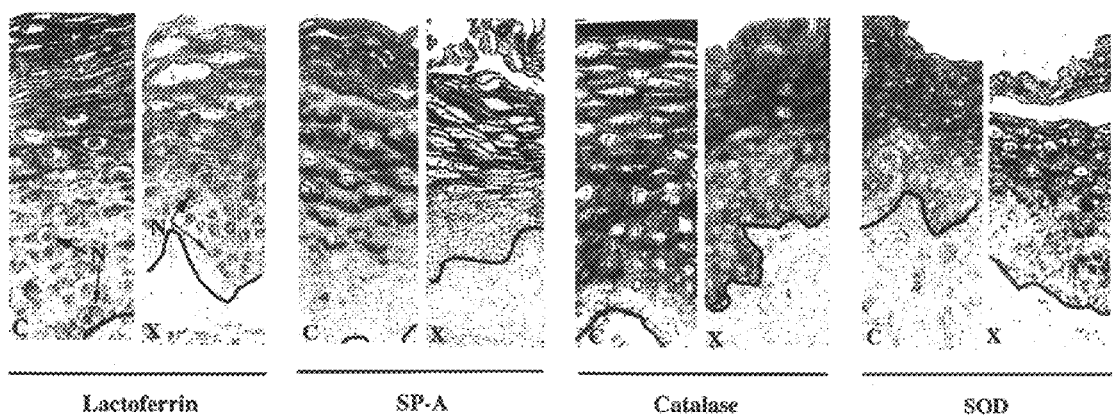
FIG. 3 presents photomicrographs (at 40X) of tissue sections from premenopausal vaginas (C), and vaginal xenografts (X) immunoreacted for LF, surfactant protein A (SP-A), catalase and SOD.

Similarly, SP-A contributes to host defenses by facilitating phagocytosis, recruiting cells in the monocyte/macrophage lineage, and thereby enhancing the immune response. Wright, J. R., et al., "Pulmonary surfactant protein A stimulates chemotaxis of alveolar macrophage." Am. J. Physiol. 264:(4 Pt 1) L338–344 (1993). As seen in FIG. 3 the distribution of imrnunoreactive SP-A is the same in normal vagina as compared to xenografts. Specifically, immunoreactive SP-A is seen in the differentiated and desquamated cell layer with localization identical to glycogen. This observation once again supports the structural and functional parity between the xenobiotic screening platform as claimed in the instant invention and normal post menopausal vaginal tissue observed in situ.

Additionally, as presented in FIG. 3, several other gene products show comparable expression between vaginal xenografts and control specimens removed from in situ vagina. Specifically, catalase, glutamyl cysteine synthase (GCS), Mn and Cu/Zn superoxide dismutases (SOD) and glutathione-S-transferase (GST). That is to say the photomicrographs of sections of premenopausal vaginal tissue, in FIG. 3, present controls (C) and vaginal xenografts (X) showing localization of immunoreactive lactofernn, surfactant protein A (SP-A), catalase and Cu/ZN superoxide dismutase (SOD) which are selected markers of host defenses. The Junction between basal epithelial cells and stroma is indicated by solid black lines.

II. Application of Candidate Antimicrobial Compounds

It is not intended that the present invention be limited to a specific protocol to administer a candidate microbicide. In one embodiment, the candidate microbicide is mixed with a given pathogen in vitro and said mixture is subsequently introduced into the lumen of the engrafted human xenograft disposed within a non-human host. In another embodiment, the candidate microbicide is pre-administered to the engrafted human vaginal lumen before the delivery of pathogens to said human vaginal lumen. In yet another embodiment, the microbicide is administered systemically and the pathogen is introduced into the lumen of the xenograft.

III. Infection of Human Vaginal Xenografts with Pathogens

While it is not intended that the screening method recited in the instant invention be limited to a specific group of pathogens, Table 2 presents examples of pathogenic agents in the screening methods recited in the instant invention. The pathology resulting from infection of xenografts with said pathogens recapitulates the pathology of the disease state observed from sections of in situ vagina infected with said pathogens. This fidelity to human pathological processes provides for the screening of candidate antimicrobials within said susceptible xenografts. That is to say, xenografts exposed to pathogens may be qualitatively or quantitatively evaluated to determine whether infected tissues recover or if infections are blocked altogether.

TABLE 2

Viruses which are pathogenic in the xenograft system

| PAPILLOMAVIRUSES | POXVIRUSES |
|---|---|
| Bovine papillomavirus (BPV-t) BPV-4 | Molluscum contagiosum |
| Cottontail rabbit papillomavirus (CRPV) HPV-1 HPV-5 HPV-11 | HERPESVIRUSES HSV-2 Varicella zoster virus |
| HPV-40 LVX82/MM7 Norwalk agent | OTHERS Vaccinia virus |

A. Inoculation of Xenografts with Pathogens

The human vaginal xenografts recited in the instant invention are obtained as specimens from surgical procedures or at autopsy, and may be prepared according to conventional techniques. In a preferred embodiment, said vaginal xenograft comprises a split-thickness graft. In one embodiment, said split thickness grafts are prepared in a substantially aseptic environment under conditions such that transplant viability in a non-human host is maximized. In one embodiment, said viability maximizing condition comprises maintaining said grafts in a culture medium (including but not limited to Minimum Essential Medium) prior to transplant. In a preferred embodiment said viability maximizing condition comprises maintaining said grafts in a culture medium (including but not limited to Minimum Essential Medium) supplemented with antibiotic to prevent subsequent bacterial infection and to control any endogenous bacterial infection in the graft.

In one embodiment a rolled split thickness human vaginal xenograft has engrafted within a host for a period of time. Preferably, said engrafting time is between approximately two and approximately fourteen days. Most preferably said engrafting time is greater than fourteen days. Subsequent to said engrafting, a given pathogen is introduced into the lumen of said engrafted rolled split thickness xenograft. Suitable instruments for the introduction of said pathogens into the lumen of said split thickness xenograft include (but are not limited to) pipet tips, syringes and swabs.

In one embodiment, the lumen of a rolled split Thickness human vaginal xenograft is inoculated with a given pathogen prior to the introduction of said inoculated xenograft into a host. Said inoculated rolled split thickness human xenograft is subsequently implanted into a host and allowed to engraft. Said inoculated engrafted tissue is permitted to remain for a period sufficient for the pathogen to multiply and a recoverable quantity of said pathogens may be produced. The grafted tissue itself may grow, become morphologically transformed, or otherwise change.

In the case of HPV, the xenograft becomes transformed by the virus. The virus grows in the xenograft in sufficient quantities for recovery in approximately 3 to 5 months after the transplantation.

IV. Detecting Pathogens in Pathogen Inoculated Human Vaginal Xenografts

Detecting residual infectivity and pathogen infiltration into the above captioned xenografts is a facet of the screening methods for candidate antimicrobial compounds contemplated by the instant invention. The present invention contemplates a variety of protocols to determine if a candidate antimicrobial compound exerts a microbicidal effect as evidenced by an absent (or diminished) residual infectivity in the pathogen inoculated grafts recited above.

In one embodiment, the polymerase chain reaction (PCR) is a protocol used to evaluate residual infectivity. PCR refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands.

The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or DATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. In this way, the presence of even a minute amount of DNA or RNA from a given pathogen, within a given pathogen inoculated human vaginal xenograft, may be documented.

In another embodiment in situ hybridization is a protocol used to evaluate residual infectivity. In this procedure, radioactive nucleic acid probes are hybridized with preparations of fixed cells rather than with purified DNA. In this way chromosomal sites of DNA or RNA of interest (e.g. pathogenic DNA or RNA) may be directly visualized by standard microscopic techniques.

In another embodiment, gel electrophoresis provides protocols used to evaluate residual infectivity. In this procedure, an extract from said inoculated human vaginal xenografts may be placed at the top of a tube or other system containing a matrix (made of polyacrylamide) and subjected to an electrical field. The rate of migration of a macromolecule (e.g., pathogen proteins) through the matrix produces characteristic bands which may be used as an index for pathogenic protein synthetic activity and, thereby, residual infectivity.

In another embodiment, immunocytochemical protocols are used to detect residual infectivity. In this method, cells are fixed briefly with alcohol (to immobilize their contents) and then treated with acetone and air-dried to disrupt plasma membranes, thereby rendering the interior of such permeabilized cells accessible to large molecules. In one embodiment, said fixed permeabilized cells may be reacted with a florescent conjugated antibody specific for a given pathogenic protein. In this way infection of said pathogen inoculated vaginal epithelium may be documented.

EXPERIMENTAL

The following examples are provided in order to demonstrate and further illustrate certain preferred embodiments and aspects of the present invention and are not to be construed as limiting the scope thereof. Although embodiments have been described with some particularity, many modifications and variations of the preferred embodiment are possible without deviating from the invention.

EXAMPLE 1

Propagation of Sexually Transmitted Fastidious Viral Pathogens

This example describes the propagation of fastidious viral pathogens. While the propagation methods recited in this example may be applied to a variety of fastidious viruses, in this example said fastidious virus is HPV. HPV is derived from infected tissue known to have detectable amounts of virus to produce an extract with a sufficient titer (number or concentration of infectious virions) to infect a susceptible tissue. Specifically, hwnan genital epithelial tissue (including the cervix) or vulvar condylomata acuminata (infected with HPV's) are preferred. Vulvar condylomata were obtained from 15 female patients and stored at −70° C. until used. A total of 20 g was thawed, minced with scissors, and disrupted in 50 ml of PBS at 4° C. with a Virtis homogenizer at 25,000 rpm for 30 minutes. Cell-free supernatants and pellets were obtained by sedimentation at 1,000× g, separated, and stored at −70° C. The supernatant was used without further dilution to infect vaginal xenografts. However, those skilled in the art will be able to adjust the titer of the above referenced supernatant to present an extract with a sufficient viral load to infect the human xenograft recited in the instant invention.

EXAMPLE 2

Construction of Split-Thickness Rolled Grafts

In this example, split thickness xenografts of human vagina are prepared according to the following method. Split thickness vaginal wall specimens were obtained from surgical sources. Vaginal wall specimens from any source were subjected to both gross and microscopic examination to confirm that said specimens were free from detectable lesions. Split-thickness grafts were created by cutting said vaginal wall specimens with a sterile double-edged razor blade clamped in a curved Kelly hemostat. Grafts were held in culture medium with only gentamicin (800 micrograms per milliliter) as supplement, and were subsequently trimmed to dimensions of 2cm×2cm×0.5 mm. Said trimmed tissue was then rolled such that an open lumen was created wherein the internal diameter of said lumen is lined with vaginal epithelium.

EXAMPLE 3

Screening of Candidate Microbicides in Vaginal Xenografts Infected with HPV

In this example, human vaginal xenografts were infected with HPV by inoculating the lumen of said vaginal xenografts, engrafted into a non-human host, with HPV-1 stock virus suspensions prepared according to the methods presented in Example 1. Experiments (data not shown) have demonstrate that even a 1:1000 dilution of said viral stock produced infections at an incidence greater than 90% in inoculated susceptible tissue. Furthermore, it is not necessary to traumatize the walls of said grafts during inoculation to precipitate infection.

In experimental samples, candidate microbicides are mixed with HPV in vitro prior to administration of said HPV/candidate microbicide mixture to the lumen of a vaginal xenograft engrafted into a non-human host. In an alternative experimental embodiment, candidate microbicides were pre-administered to the vaginal lumen, before delivery of a pathogenic agent, into the same lumen.

Xenografts are harvested at 70–90 days and are screened for signs of virus replication. Said screening protocols include quantification of morphologic transformations, viral DNA and RNA synthesis, and protein synthesis. In addition, cell-free extracts of infected xenografts are tested by bioassay for the presence of infectious virus using standard procedures for infection and transformation of vaginal epithelium.

EXAMPLE 4

Screening of Candidate Microbicides in Vaginal Xenografts Infected with HIV

In this example, human vaginal xenografts are infected with HIV by inoculating the lumen of said vaginal xenografts, engrafted into a non-human host, with HIV stock virus suspensions. HIV viral strains tested include lymphocytotrophic strains, HIV-1 strain III B and MN, and monocytotrophic strains Bal and ADA, as well as dual trophic strain 89.6. Virus preparations may be obtained from commercial sources including Advanced Biotechnologies (Rockville, Md.).

In experimental samples, candidate microbicides are mixed with IV in vitro prior to administration of said HIV/candidate microbicide mixture to the lumen of an vaginal xenograft engrafted into a non-human host. In an alternative embodiment, candidate microbicides are pre-administered to the vaginal lumen prior to delivery of HIV suspensions into the same lumen.

Xenografts are harvested at different intervals and assayed for virus macromolecules and virus yield, according to methods well known in the art, to determine if HIV infection has occurred.

EXAMPLE 5

Screening of Candidate Microbicides in Vaginal Xenografts Infected with HIV Infected Cells Purified viral suspensions of HIV may also be used to initiate infections of cells in culture and these infected cells are then transferred into the lumen of vaginal xenografts engrafted into a non-human host.

For the lymphocytotrophic strains of HEIV, infections are initiated in SUP T or JURKAT cells. Smith, S. D., et al., "Monoclonal antibody and enzymatic profiles of human malignant T-lymphoid cells and derived cell lines.", Cancer Res. 44:5657–5660 (1984), Gillis, S., et al., "Biochemical and biological characterization of lymphocyte regulatory molecules. V. Identification of an interleukin 2-producing human leukemia T cell line." J. Exp. Med. 152:1709–1719 (1980). For monocytotrophic strains HIV, infections are initiated in THP-1 or U937 cells. Tsuchiya, S., et. al., "Establishment and characterization of a human acute monocytic leukemia cell line (THP-1)." Int. J. Cancer 26:171–176 (1980), Sundstrom, C., et al., "Establishment and characterization of a human histiocytic lymphoma cell line (U937)." Int. J. Cancer 17:565–577 (1976). Additionally, infections with one or both types of HIV strains are initiated in peripheral blood leukocytes. In each scenario, the above referenced in vitro HIV infected cells are monitored for the synthesis of new HIV progeny.

At times, corresponding to a peak of virus replication in said in vitro HIV inoculated cells, infected cells are transferred to the xenografts. The fate of the inoculated cells are evaluated histologically for the presence of viable lymphoreticular cells.

In experimental samples, candidate microbicides are mixed with said HIV inoculated cells in vitro prior to administration of said HIV inoculated cell/candidate microbicide mixture to the lumen of a vaginal xenograft engrafted into a non-human host. In an alternative embodiment, candidate microbicides are pre-administered to the vaginal lumen, before delivery of said HIV inoculated cells, into the same lumen.

EXAMPLE 6

Screening of Candidate Microbicides in Vaginal Xenografts Inoculated with C. Trachomatis In this example, human vaginal xenografts are infected with C. trachomatis by inoculating the lumen of said vaginal xenografts, engrafted into a non-human host, with a culture of C. trachomatis.

In experimental samples, candidate rnicrobicides are mixed with C. trachomatis in vitro prior to administration of said C. trachomatis/candidate microbicide mixture to the lumen of a vaginal xenograft engrafted into a non-human host. In an alternative embodiment, candidate microbicides are pre-administered to the vaginal lumen, before delivery of a culture of C. trachomatis, into the same lumen.

Quantitation of C. trachomatis survival following microbicide exposure is accomplished by in vitro assay of C. trachomatis survival in xenograft ravages or extracts.

EXAMPLE 7

Use of Sodium Dodecyl Sulfate (SDS) as a Candidate Microbicide In The Instant Screening System In this example, human vaginal xenografts engrafted for ten days in the subcutaneous space of an immunocompromised mouse were infected with 10 ul of HPV-11, or HPV-11 that had been treated with 0.05% SDS at 37° C. for 10 minutes and then placed in the lumen of the grafts. At varying intervals, the infected human xenografts (or portions thereof) were surgically removed and examined. These infected tissues exhibited papillomatous transformations with the elaboration of abundant virus DNA and virus protein demonstrating virion production.

Figure 4:
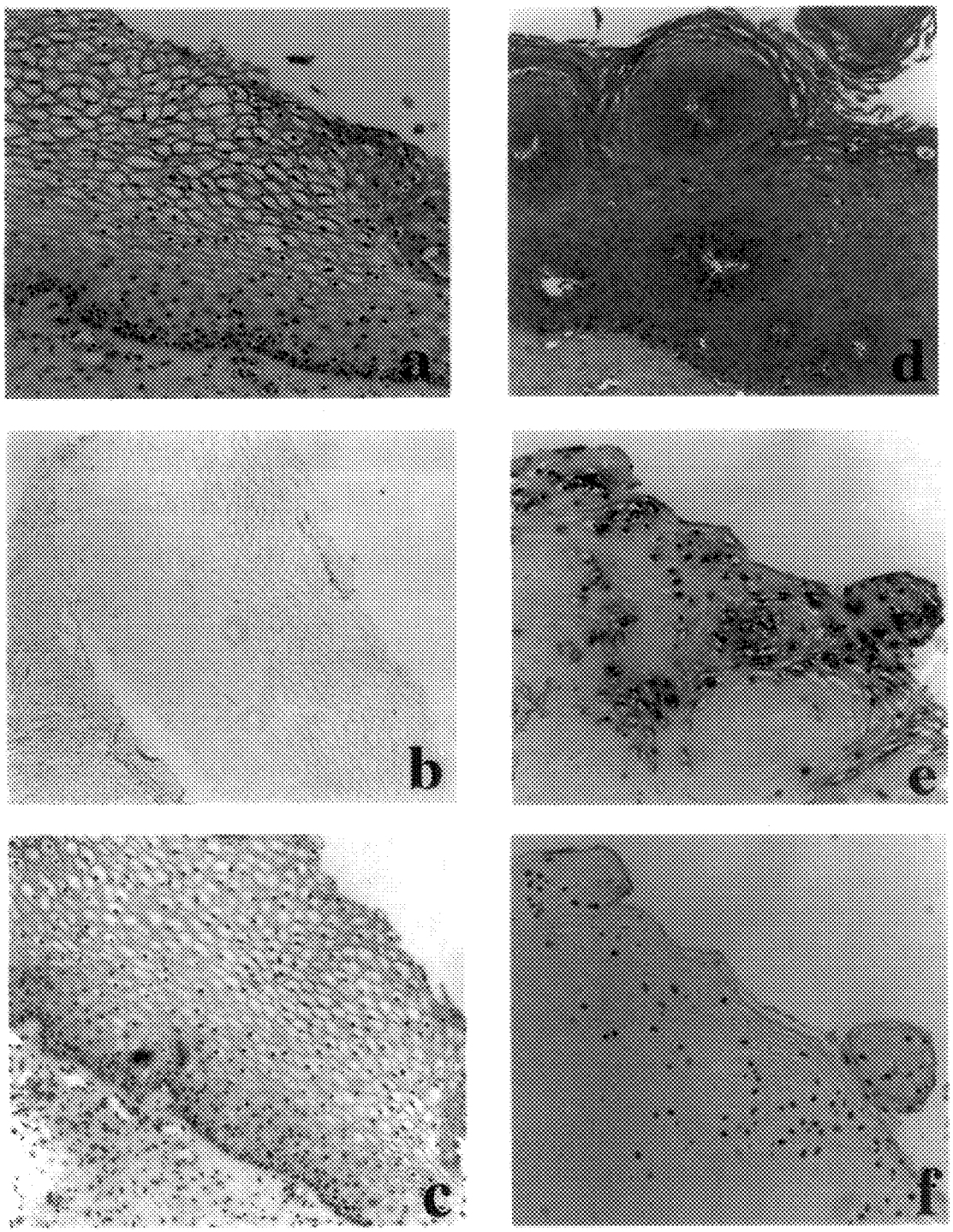
FIGS. 4A–F presents photomicrographs of harvested grafts which received Sodium Dodecyl Sulfate (SDS)-treated virus (panels a, b and c) or untreated virus (panels d, e, and f). Panels a and d represent hematoxylin and eosin stained tissues, panels b and e show hybridization of HPV-11 DNA probe and panels c and f show GSA staining for HPV protein.

This pathological morphology and physiology was not seen in tissues receiving SDS-treated virus and these samples exhibited stratified squamous epithelium with a morphology analogous to normal in situ vagina. Indeed, as illustrated in FIG. 4 the SDS effectively prevented virus infection but did not kill the treated epithelium in the vaginal xenograft.

EXAMPLE 8

Assay of Xenografts for Infection by Pathogens

The human vaginal xenografts recited in the instant invention may be recovered and assayed for pathogenic infection any time after the inoculation of pathogens. Recovery may be effected by sacrificing the animal and removing the tissue, from which the pathogen may be extracted by known techniques. Alternatively, the virus may be recovered while the tissue remains in the living animal through known techniques, such as surgical removal of part or all of the xenograft tissue.

It is not intended the present invention be limited to a specific assay or technique to evaluate whether a human vaginal xenograft has been infected with a given pathogen. There are a number of standard culture techniques for infectivity, including but not limited to, quantitative colony cultureon agar plates (for bacteria) and quantitative plaque assays (for viruses).

In one embodiment (where the pathogen contacted to said vaginal xenograft is a virus) the tissue is homogenized, said homogenate is subjected to centrifugation using cesium chloride density gradients to cause sedimentation of the virus particles. Under these conditions, viral particles localize as a homogeneous band or bands at those densities which correspond to its buoyant density. In the example of HPV this is at approximately 1.34 g/cc and slightly above.

In another embodiment, said pathogen assay technique is PCR. In another embodiment, said pathogen assay technique is in situ hybridization. In another embodiment said pathogen assay technique is protein staining. In another embodiment, said pathogen assay technique is gel electrophoresis. In another embodiment, said pathogen assay technique is immunocytochemistry.

From the above, it is clear the present invention provides compositions and methods for the screening of candidate microbicides. In particular, the present invention provides a human vaginal xenograft, engrafted into a non-human host, as a platform for screening the efficacy of topically applied candidate antimicrobial agents against pathogens of interest including (but not limited to) HSV-2, HPV, HIV, and *C. trachomatis*.

All publications and patents mentioned in the above specification are herein incorporated by reference. Although the invention has been described in connection with specific preferred embodiments, it should be understood that the invention as claimed should not be limited to such specific embodiments. Indeed, various modifications of the described modes for calying out the invention which are obvious to those skilled in the art are intended to be within the scope of the following claims.

What is claimed is:

1. A method for screening compounds, comprising:
   a) providing: i) an immunocompromised non-human host; ii) a human vaginal graft comprising a lumen; iii) a candidate compound; and iv) a pathogen;
   b) engrafting said vaginal graft within said host to create an engrafted vaginal xenograft comprising a lumen;
   c) introducing said compound systemically into said non-human host;
   d) inoculating said engrafted vaginal xenograft with said pathogen; and
   e) testing said engrafted vaginal xenograft for the presence of pathogen.

2. The method of claim 1, wherein said inmuunocompromised non-human host is a vertebrate.

3. The method of claim 1, wherein said human vaginal graft comprises a split thickness graft.

4. The method of claim 3, wherein said split thickness graft was configured to create a lumen, wherein said lumen is substantially lined with epithelial cells.

5. The method of claim 1, wherein said pathogen is selected from bacteria, fungi, parasites, and viruses.

6. The method of claim 5, wherein said viruses are selected from the group consisting of HSV-2, HPV, and HIV.

7. The method of claim 1, wherein, after said engrafting of step (b), said host is administered one or more gonadal hormones.

8. A method for screening compounds, comprising:
   a) providing: i) an immunocompromised non-human host; ii) a human vaginal graft comprising a lumen; iii) a candidate compound; and iv) a pathogen;
   b) engrafting said vaginal graft within said host to create an engrafted vaginal xenograft comprising a lumen;
   c) inoculating said engrafted vaginal xenograft with said pathogen;
   d) introducing said compound systemically into said non-human host; and
   e) testing said engrafted vaginal xenograft for the presence of pathogen.

9. The method of claim 8, wherein said immunocompromised non-human host is a vertebrate.

10. The method of claim 8, wherein said human vaginal graft comprises a split thickness graft.

11. The method of claim 10, wherein said split thickness graft was configured to create a lumen, wherein said lumen is substantially lined with epithelial cells.

12. The method of claim 8, wherein said pathogen is selected from bacteria, fungi, parasites, and viruses.

13. The method of claim 12, wherein said viruses are selected from the group consisting of HSV-2, HPV, and HIV.

14. The method of claim 8, wherein, after said engrafting of step (b), one or more gonadal hormones is administered to said host.

15. The method of claim 14, wherein said hormone is selected from the group consisting of $\beta$-estradiol and progesterone.

* * * * *

UNITED STATES PATENT AND TRADEMARK OFFICE
CERTIFICATE OF CORRECTION

PATENT NO. : 6,309,848 B1
DATED : October 30, 2001
INVENTOR(S) : Mary K. Howett and John W. Kreider It is certified that error appears in the above-identified patent and that said Letters Patent is hereby corrected as shown below:

Column 1,
Line 6, insert the following paragraph:
-- This invention was made with support from the United States Government under NIAID Grant No. N01-Al-35158. The Government has certain rights in the invention. --

Signed and Sealed this

Eighth Day of February, 2005

JON W. DUDAS
*Director of the United States Patent and Trademark Office*